United States Patent [19]

Jung et al.

[11] 4,135,909
[45] Jan. 23, 1979

[54] SALTS OF PHOSPHONIC ACIDS

[75] Inventors: Johann Jung, Limburgerhof; Karl Kiehs, Lampertheim; Bernd Zeeh, Ludwigshafen; Hans Theobald, Limburgerhof, all of Fed. Rep. of Germany

[73] Assignee: BASF Aktiengesellschaft, Ludwigshafen, Fed. Rep. of Germany

[21] Appl. No.: 755,581

[22] Filed: Dec. 29, 1976

Related U.S. Application Data

[62] Division of Ser. No. 568,147, Apr. 14, 1975, Pat. No. 4,071,551.

[30] Foreign Application Priority Data

May 10, 1974 [DE] Fed. Rep. of Germany ....... 2422807

[51] Int. Cl.$^2$ .......................... C07F 9/38; A01N 9/36
[52] U.S. Cl. ........................................ 71/86; 544/108; 546/184
[58] Field of Search ............... 260/247, 293.51; 71/86, 71/94; 544/108

[56] References Cited

U.S. PATENT DOCUMENTS

| 3,808,265 | 4/1974 | Randall et al. ................. 260/502.4 R |
| 3,819,353 | 6/1974 | Langsdorf ................................ 71/86 |

FOREIGN PATENT DOCUMENTS 6802633 8/1968 Netherlands ................................. 71/86

*Primary Examiner*—Henry R. Jiles
*Assistant Examiner*—R. W. Ramsuer
*Attorney, Agent, or Firm*—Keil, Thompson & Shurtleff

[57] ABSTRACT

New and valuable salts of phosphonic acids whose cationic components are ammonium radicals, agents for influencing the growth of plants with these salts, and a process for their manufacture.

2 Claims, No Drawings

SALTS OF PHOSPHONIC ACIDS

This is a division of application Ser. No. 568,147 filed Apr. 14, 1975, now U.S. Pat. No. 4,071,551.

The present invention relates to new salts of phosphonic acids whose cationic components are ammonium radicals, agents containing these salts for influencing plant growth, and a process for producing these compounds.

It is known that phosphonic acids (Dutch Pat. No. 1,668,075, German LaidOpen Application DOS 1,916,147) and ammonium salts (U.S. Pat. No. 3,230,069, Dutch Application No. 6,516,589 and French Pat. No. 1,461,144) have an influence on plant growth.

We have now found that salts of phosphonic acids of the formula

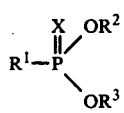

where X denotes sulfur or oxygen, $R^1$ denotes linear or branched alkyl, alkenyl or alkynyl of 1 to 12 carbon atoms which may be substituted by 1 or more halogen atoms, or benzyl or naphthyl which may be substituted by one or more halogen atoms, amino, alkylamino, dialkylamino or nitro groups, and $R^2$ and $R^3$ denote, independently of each other, hydrogen, alkyl of a maximum of 12 carbon atoms which may be substituted by halogen and at least one of $R^2$ and $R^3$ denotes a radical of the formula

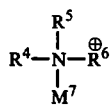

where $R^4$ denotes alkyl of a maximum of 6 carbon atoms or amino, and $R^5$, $R^6$ and $R^7$, independently of each other, denote hydrogen, linear or branched, cyclic or non-cyclic alkyl, alkenyl or alkynyl of a maximum of 12 carbon atoms which may be substituted by one or more halogen atoms, oxirane or oxiranealkyl of a maximum of 6 carbon atoms, or $R^6$ and $R^7$ together form a heterocyclic ring, e.g., pyrrolidione, piperidine, morpholine, hexahydropyridazine and tetrahydropyridazine, have a powerful effect on plant growth.

The action of the new active ingredient is similar to that of quaternary nitrogen compounds and various phosphonic acid derivatives. However, at the same application rates the action of the new compounds is generally much more marked, quite apart from the fact that the spectrum of action is much broader. Plant growth responses caused by the compounds of the invention are in particular the following:

Reduction of stem or stalk length, thus increasing the resistance to lodging of barley, oats, rye, wheat, Indian corn, soybeans and cotton.

Abscission of foliage, flowers and fruit, e.g., in olives and tree nursery plants.

Promotion of ripening, for instance in tomatoes, citrus fruits and bananas.

Increase in yield, particularly in cereals and legumes.

The new active ingredients may be applied to the foliage and stems of the plants, and to the soil in which the plants are growing, or as seed dressings; they are in all cases effective, regardless of the application method employed. It is also possible to combine the compounds of the invention with other active ingredients, especially plant protection agents, and fertilizers and inert carriers. The addition of wetting agents usually fortifies the action.

The new salts according to the invention may for instance be prepared as follows:

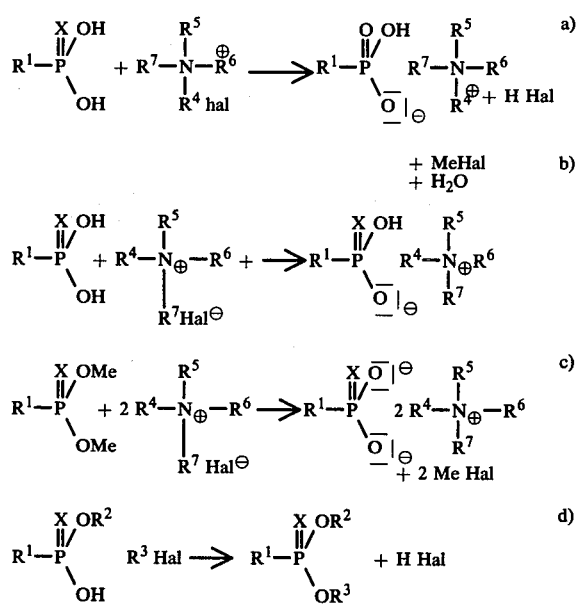

$R^1$, $R^2$, $R^3$, $R^4$, $R^5$, $R^6$ and $R^7$ have the above meanings, Hal denotes halogen and Me stands for a metal atom, e.g., alkali metal, alkaline earth metal or an ammonium ion.

The hydrogen halide liberated in the above reactions may be removed from the reaction mixture for instance by introducing gases, e.g., nitrogen, oxygen, and carbon dioxide, by conventional acid binding agents, e.g., amines, especially tertiary amines such as triethylamine, or by employing metal hydroxides (e.g., alkali metal hydroxides and alkaline earth metal hydroxides), metal carbonates, metal hydrogen carbonates, alcoholates, and ammonium or metal salts of phosphonic acids.

The reaction of free phosphonic acid with a substituted ammonium halide is preferred.

The above reactions are advantageously carried out in diluents, the following being suitable examples: alcohols, e.g., methanol, ethanol and propanol; nitriles such as acetonitrile and propionitrile; ketones, e.g., acetone and methyl ethyl ketone; water, benzene, toluene, chlorobenzene, xylenes, chlorinated hydrocarbons such as methylene chloride, chloroform and carbon tetrachloride; dimethyl sulfoxide, dimethylformamide and other solvents. Most suitable are solvents enabling the desired phosphonic acid salt to be separated direct from any inorganic reaction products which may be obtained, e.g., alcohols, ketones and nitriles.

The reactions may be carried out over a wide temperature range of from $-10°$ C. to the decomposition point of the reactants and end products ($+250°$ C.).

The preparation of the compounds of the invention is illustrated by the following examples. The salts are identified by their nmr spectra.

EXAMPLE 1

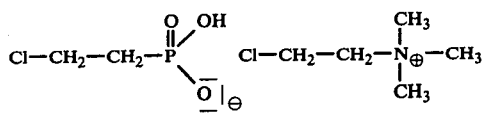

At 50° C., 5.6 parts (by weight) of potassium hydroxide in 50 parts of ethyl alcohol was added to a solution of 14.4 parts of 2-chloroethanephosphonic acid and 15.7 parts of chlorocholine chloride in 100 parts of ethyl alcohol. The mixture was stirred for 3 hours at 70° C. and cooled. The precipitate was separated by filtration. The filtrate was concentrated and recrystallized from a mixture of methanol and ligroin. The melting point was 86° to 87° C. and the yield 25.4 parts (95.5% of theory). $C_7H_{18}Cl_2NO_3P$ (266)

|        | C    | H   | N   | P    | Cl   |
|--------|------|-----|-----|------|------|
| Calc.: | 31.6 | 6.8 | 5.3 | 11.6 | 26.7 |
| Found: | 31.2 | 6.5 | 5.0 | 11.7 | 26.3 | nmr (δ values) at 60 mc/sec: 3.5–4.05 (6 H), 3.2 (9 H), 2.17 (2 H).

EXAMPLE 2

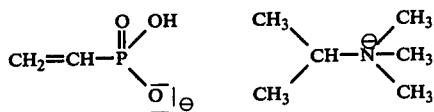

At 20° C., 6.8 parts of sodium ethylate in 50 parts of ethanol was added to a solution of 10.8 parts of vinylphosphonic acid and 13.75 parts of isopropyl trimethylammonium chloride in 80 parts of ethanol. The mixture was then stirred for 5 hours at 70° C. and worked up as in Example 1. The yield was 19.9 parts (95% of theory). $C_8H_{20}NPO_3$ (209)

|        | C    | H   | N   | P    |
|--------|------|-----|-----|------|
| Calc.: | 45.9 | 9.6 | 6.7 | 14.8 |
| Found: | 45.6 | 9.6 | 6.9 | 14.7 | nmr (δ values) at 60 mc/sec: 5.2–6.25 (3 H), 3.62 (H), 3.02 (9 H), 1.36 (6 H).

EXAMPLE 5

3.92 parts of potassium hydroxide in 50 parts of ethanol was added to a solution of 10.1 parts of 2-chloroethanephosphonic acid in 80 parts of ethanol. After the mixture had been stirred for 1 hour at 40° C. the solvent was distilled off. The residue was taken up in 150 parts of acetonitrile and 13.6 parts of N,N-dimethylpiperidinium bromide was added to the mixture. The reaction mixture was stirred for 5 hours at 70° C. and then cooled. The precipitates was filtered off and the filtrate concentrated. The yield was 17.5 parts (97% of theory).

| $C_9H_{21}NPO_3Cl$ (257.5) | C | H | N | P | Cl |
|---|---|---|---|---|---|
| Calc.: | 42.0 | 8.2 | 5.4 | 12.1 | 13.8 |
| Found: | 41.8 | 8.1 | 5.5 | 12.4 | 13.9 | nmr spectra (δ values) at 60 mc/sec: 3.77 (2H), 3.32 (4H), 3.09 (6H), 2.14 (2H), 1.6–1.95 (4H), 1.7 (2H).

The following salts were prepared in similar manner:

-continued

| Structure | Structure | Data |
|---|---|---|
| Cl—CH₂—CH₂—P(=O)(O⁻)(O—CH₂—CH₂—Cl) | Cl—CH₂—CH₂—N⁺(CH₃)₃ | 3.3–4.2 (10 H), 3.09 (9 H), 2.05 (2 H) |
| naphthyl-CH₂—P(=O)(OH)(O⁻) | Cl—CH₂—CH₂—N⁺(CH₃)₃ | characteristic infrared bands (cm⁻¹) 1650, 1475, 1150, 1050, 945, 915, 775, 490 |
| CHCl₂—CH₂—P(=O)(OH)(O⁻) | Cl—CH₂—CH₂—N⁺(CH₃)₃ | characteristic infrared bands (cm⁻¹) 1640, 1480, 1185, 1160, 1050, 940, 910, 530 |
| CH₂=CH—P(=O)(OH)(O⁻) | Cl—CH₂—CH₂—N⁺(CH₃)₃ | 5.6–6.3 (3 H), 3.23 (9 H), 4.02 (2 H), 3.82 (2 H) |
| Cl—CH₂—CH₂—P(=O)(OH)(O⁻) | (CH₃)₂N⁺(CH₂)₃NH (cyclic) | 1.72 (2 H), 2.02 (2 H), 2.19 (2 H), 3.18 (2 H), 3.34 (6 H), 3.52 (2 H), 3.78 (2 H) |
| Cl—CH₂—CH₂—P(=O)(OH)(O⁻) | Cl—CH₂—CH₂—N⁺(CH₃)₃ | 2.21 (2 H), 3.45 (6 H), 3.79 (2 H), 3.9–4.1 (4 H) |
| (CH₃)₂C=CH—P(=O)(OH)(O⁻) | N-methylmorpholinium | |
| CH₂=CH—CH₂—P(=O)(OH)(O⁻) | N,N,N-trimethylcyclopentylammonium | |
| (CH₃)₂CH—CH=CH—P(=O)(OH)(O⁻) | (CH₃)₂CH—N⁺(CH₃)₃ | |
| Cl—CH₂—CH₂—P(=O)(OH)(O⁻) | CH₂=CH—CH₂—N⁺(CH₃)₂(NH₂) | |
| 4-Cl-C₆H₄—CH₂—P(=O)(OH)(O⁻) | CH₂=C(Cl)—CH₂—N⁺(CH₃)₃ | |
| Cl—CH₂—CH₂—P(=O)(OH)(O⁻) | (CH₃)₂N⁺—CH₂—CH(—CH₂—)O (epoxide) | |
| CH₂=CH—P(=O)(OH)(O⁻) | (CH₃)₂N⁺-cyclic with N | |

The growth-regulating properties of the compounds according to the invention may be extended by adding other growth regulators and adapted to suit prevailing conditions by mixing them with fungicides and fertilizers, especially urea. The ratio of the salts of the invention to growth regulators, fungicides and fertilizers in such compositions may be varied at will; what type of composition is used depends on the conditions encountered (fungus diseases, deficiencies, etc.).

Examples of growth regulators which may be mixed with the salts of the invention are:
phosphonic acids and their derivatives, such as
2-chloroethanephosphonic acid
vinylphosphonic acid propylphosphonic acid
phosphonomethylglycine
bisphosphonomethylglycine
benzylphosphonic acid
ammonium and hydrazinium salts, such as
chlorocholine hydrochloride
N,N-dimethylmorpholinium halide
N,N-dimethyl-N-2-chlorpethylhydrazinium halide
N,N-dimethyl-N-2-bromoethylhydrazinium halide
N,N-dimethyl-N-isopropylhydrazinium halide
N,N-dimethyl-N-propen-(2)-ylhydrazinium halide
N,N,N-trimethyl-N-cyclopropanemethylammonium halide
N,N-dimethylhexahydropyridazinium halide
N,N-dimethyltetrahydropyridazinium halide
N,N,N-trimethyl-N-cyclopentenylammonium halide
N,N-dimethyl-N-cyclopentenylhydrazinium halide
N,N,N-trimethyl-N-isopropylammonium halide
carboxylic acid and derivatives thereof, such as
β-indolylacetic acid
α-naphthylacetic acid
4-chlorophenoxyacetic acid
2,4-dichlorophenoxyacetic acid
2-methyl-4-chlorophenoxyacetic acid
2,4,5-trichlorophenoxyacetic acid
α-(2-methylphenoxy)-propionic acid
α-(2,4-dichlorophenoxy)-propionic acid
α-(2-methyl-4-chlorophenoxy)-propionic acid
α-(2,4,5-trichlorophenoxy)-propionic acid
γ-(2,4-dichlorophenoxyl-butyric acid
γ-(2-methyl-4-chlorophenoxy)-butyric acid
2,4,5-triiodobenzoic acid
sulfonium salts, such as
S,S-dimethyl-S-2-chloroethylsulfonium halide
S,S-dimethyl-S-isopropylsulfonium halide
S-methylthianium halide
1-methyl-1,4-dithianium halide
heterocyclic structures, such as
maleic hydrazide
succinic acid-N,N-dimethylhydrazide
N-formyl-N-hydroxyglycine and salts
9-hydroxyfluorene-9-carboxylic acid
7-chloro-9-hydroxyfluorene-9-carboxylic acid citric hydrazide
5-chloro-2-thienylmethyl tri-n-butylphosphonium halide Examples of fungicides capable of combination with the compounds of the invention are
dithiocarbamates and derivatives thereof, e.g.,
ferric dimethyldithioacrbamate (ferbam)
zinc dimethyldithiocarbamate (ziram)
manganese ethylenebisdithiocarbamate (maneb)
zinc ethylenebisdithiocarbamate (zineb)
tetramethylthiuram disulfide (thiram)
3,5-dimethyl-1,3,5-2H-tetrahydrothiadiazine-2-thione
nitrophenol derivatives, such as
dinitro-(1-methylheptyl)-phenylcrotonate (dinocap)
2-sec-butyl-4,6-dinitrophenyl-3,5-dimethylacrylate (binapacryl)
2-sec-butyl-4,6-dinitrophenylisopropylcarbonate
heterocyclic structures, such as
N-trichloromethylthiotetrahydrophthalimide (captan)
N-trichloromethylthiophthalimide (folpet)
2-heptadecyl-2-imidazoline (glyodin)
2,4-dichloro-b-(o-chloroanilino)-s-triazine
diethylphthalimido thiophosphate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone (dithianon)
2-thio-1,3-dithio-[4,5-b]-quinoxaline (thioquinox)
methyl-1-(butylcarbamoyl)-2-benzimidazolecarbamate
2-methoxycarbonylaminobenzimidazole
2-thiocyanomethylthiobenzothiazole (busan)
4-(2-chlorophenylhydrazono)-3-methyl-5-isooxadolone
pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxyanilido-6-methyl-1,4-oxathiin 5,5-dimetyyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene (thiophanat)
1,2-bis-(3-methoxycarbonyl)-2-thioureido-benzene
and various fungicides, such as
dodecylguanidine acetate (dodine)
3-[2-(3,5-dimethyl-2-oxycyclohexyl)-2-hydroxyethyl]-glutarimide (cycloheximide)
hexachlorobenzene
2,5-dimethylfuran-3-carboxanilide
2,5-dimethylfuran-3-carboxylic acid cyclohexylamide
2-methylbenzanilide
2-iodobenzanilide
2,3-dihydro-6-methyl-1,4-oxathiin-5-carboxanilide
2,3-dihydro-4,4-dioxy-1,4-oxathiin-5-carboxanilide
2,6-dimethyl-N-tridecylmorpholine and salts thereof
2,6-dimethyl-N-cyclodecylmorpholine and salts thereof 2,3-dichloro-1,4-naphthoquinone
1,4-dichloro-2,5-dimethoxybenzene
p-dimethylaminobenzenediazosodium sulfonate
2-chloro-1-nitropropane
N-(1,1,2,2-tetrachloroethylthio)-tetrahydrophthalimide
N,N-dimethyl-N-phenyl-(N-fluorodichloromethylthio)-sulfamide
N-methyl-N-phenyl-(N'-fluorodichloromethylthio)-N'-methylsulfamide
polychloronitrobenzenes, such as pentachloronitrobenzene, methyl isothiocyanate, fungicidal antibiotics such as griseofulvin and kasugamycin, tetrafluorodichloroacetone, 1-phenylthio semicarbazide, Bordeaux mixture, nickel-containing compounds and sulfur manganese-zinc ethylenediamine-bisdithiocarbamate zinc-(N,N'-propylene-1,2-bisdithiocarbamate) ammonia complex of zinc-(N,N'-ethylene-bisdithiocarbamate) and N,N'-polyethylene-bis-(thiocarbamoyl)-disulfide ammonia complex of zinc-(N,N'-propylene-bisdithiocarbamate) and N,N'-polypropylene-bis-(thiocarbamoyl)-disulfide.

EXAMPLE 4

Action on cotton

Cotton plants grown in the greenhouse were sprayed at a growth height of from 10 to 12 cm with formulations of the active ingredients. The application rate was 6 mg per vessel, corresponding to 6 kg per hectare. 18 days later the growth was measured and the absolute and relative height compared with control plants was determined.

| | Growth height | |
|---|---|---|
| | absolute | relative |
| Control | 29.5 | 100 |
| Cl—CH$_2$—CH$_2$—P(=O)(OH)(OH) | 28.0 | 94.9 |
| [Cl—CH$_2$—CH$_2$—N$^\pm$(CH$_3$)$_2$(CH$_3$)] | 19.0 | 64.4 |
| 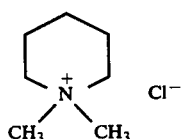 | 17.3 | 58.6 |
| 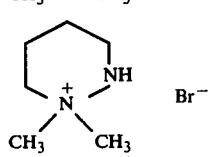 | 22.3 | 75.6 |
| Cl—CH$_2$—CH$_2$—P(=O)(OH)(O$^-$) · [N(CH$_3$)$_2$-piperidinium]$^+$ | 16.0 | 54.2 |

EXAMPLE 5

Action on rye

Rye grains of the Petkuser variety were sowed in loamy sandy soil contained in pots. The active ingredients were applied in aqueous solution to the surface of the soil immediately after the grains had been sown in amounts of 3 mg per vessel, equivalent to 3 kg per hectare. The experiment was conducted in the greenhouse. The growth height after 24 days is apparent from the following table:

| | Growth height | |
|---|---|---|
| | absolute | relative |
| Control | 30.5 | 100 |
| [Cl—CH$_2$—CH$_2$—N$^\pm$(CH$_3$)$_2$CH$_3$] Cl$^-$ | 30.0 | 98.4 |
| Cl—CH$_2$—CH$_2$—P(=O)(OH)(OH) | 30.0 | 98.4 |
| Cl—CH$_2$—CH$_2$—P(=O)(O$^-$)(O$^-$) · Cl—CH$_2$—CH$_2$—N$^\pm$(CH$_3$)$_3$ | 26.0 | 85.2 |

At an application rate of 12 mg/pot (= 12 kg/ha) and under otherwise the same conditions, the following action was observed:

| | Growth height | |
|---|---|---|
| | absolute | relative |
| Control | 28.9 | 100 |
| [Cl—CH$_2$—CH$_2$—N$^\pm$(CH$_3$)(NH$_2$)CH$_3$] Cl$^-$ | 27.0 | 93.0 |
| Cl—CH$_2$—CH$_2$—P(=O)(OH)(OH) | 29.0 | 100 |
| Cl—CH$_2$—CH$_2$—P(=O)(OH)(O$^-$) · Cl—CH$_2$—CH$_2$—N$^\pm$(CH$_3$)(NH$_2$)CH$_3$ | 24.5 | 85.0 |

EXAMPLE 6

Action on wheat

The active ingredients according to the invention were tested on wheat of the Opal variety under the same conditions as in Example 5. The application rate was 12 mg/pot (= 12 kg/ha). The stalks had the following lengths 21 days after sowing:

|  | Growth height | |
|---|---|---|
|  | absolute | relative |
| Control | 35.3 | 100 |
| [Cl—CH₂—CH₂—N±(CH₃)₃] Cl⁻ | 26.0 | 73.7 |
| Cl—CH₂—CH₂—P(=O)(OH)₂ | 29.5 | 83.6 |
| Cl—CH₂—CH₂—P(=O)(OH)(O⁻)  Cl—CH₂—CH₂—N±(CH₃)₃ | 23.5 | 66.6 |
| Cl—CH₂—CH₂—P(=O)(O⁻)₂  Cl—CH₂—CH₂—N±(CH₃)₃ | 23.5 | 66.6 |

EXAMPLE 7

Action on barley

Barley plants were grown in pots in the open with a controlled water supply, and sprayed in the 3- to 4-leaf stage with aqueous formulations of the active ingredients. The application rate was 3 kg/ha. The influence of the active ingredients on stalk length (up to ripeness) is apparent from the following table:

|  | Growth height | |
|---|---|---|
|  | absolute | relative |
| Control | 70.8 | 100 |
| [Cl—CH₂—CH₂—N±(CH₃)₃] Cl⁻ | 65.7 | 93.5 |
| N,N-dimethylpiperidinium Cl⁻ | 69.3 | 97.9 |
| 3-NH piperidinium (N,N-dimethyl) Br⁻ | 70.5 | 99.6 |
| Cl—CH₂—CH₂—P(=O)(OH)(O⁻) · N,N-dimethylpiperidinium | 65.0 | 91.8 |

EXAMPLE 8

Action on rye

Rye plants in the 3- to 4-leaf stage were sprayed under the same conditions as in Example 7 at application rates of 3 kg/ha. The results are given below:

|  | Stalk length | |
|---|---|---|
|  | absolute | relative |
| Control | 135.2 | 100 |
| [Cl—CH₂—CH₂—N±(CH₃)₃] Cl⁻ | 127.7 | 94.5 |
| N,N-dimethylpiperidinium Cl⁻ | 129.8 | 90.0 |
| 3-NH piperidinium (N,N-dimethyl) Br⁻ | 128.2 | 94.8 |
| Cl—CH₂—CH₂—P(=O)(OH)(O⁻) · N,N-dimethylpiperidinium | 116.3 | 86.0 |
| Cl—CH₂—CH₂—P(=O)(OH)(O⁻) · 3-NH-N,N-dimethylpiperidinium | 120.7 | 89.3 |

EXAMPLE 9

Action on Indian Corn

Indian corn plants were grown in pots under the same conditions as in Examples 7 and 8. The active ingredients were applied to the leaves at a plant height of from 20 to 24 cm and at a rate of 3 kg/ha. The growth height was measured after 7 weeks:

|  | Growth height | |
|---|---|---|
|  | absolute | relative |
| Control | 111.3 | 100 |

-continued

| Compound | Growth height absolute | Growth height relative |
|---|---|---|
| [Cl—CH$_2$—CH$_2$—N$^+$(CH$_3$)$_3$] Cl$^-$ | 108.5 | 97.5 |
| Cl—CH$_2$—CH$_2$—P(=O)(OH)$_2$ | 108.3 | 97.3 |
| Cl—CH$_2$—CH$_2$—P(=O)(OH)(O$^-$) | — | — |
| [Cl—CH$_2$—CH$_2$—N$^\pm$(CH$_3$)$_3$] | 99.8 | 89.7 |
| Cl—CH$_2$—CH$_2$—P(=O)(OH)(O$^-$) · piperidinium-N,N-dimethyl | 102.3 | 91.9 |

EXAMPLE 10

Action on oats

Oat plants were grown in loamy sandy soil contained in pots in a greenhouse. The plants were sprayed at a height of from 10 to 12 cm with the active ingredients at a rate corresponding to 6 kg/ha. The following results were obtained after 15 days:

| | Growth height absolute | Growth height relative |
|---|---|---|
| Control | 29.5 | 100 |
| [Cl—CH$_2$—CH$_2$—N$^\pm$(CH$_3$)$_3$] Cl$^-$ | 24.5 | 83.1 |

| Compound | Growth height absolute | Growth height relative |
|---|---|---|
| CH$_2$=C(H)—P(=O)(OH)(O$^-$) · [Cl—CH$_2$—CH$_2$—N$^+$—(CH$_3$)$_3$] | 23.5 | 79.7 |

EXAMPLE 11

Action on cress 40 cress seeds for each experiment were placed on filter paper, which was then introduced into a beaker containing 20 ml of active ingredient formulation. After 4 days the length of the plants was measured and calculated in percent of the growth of the untreated control. The figure 100% denotes no stunting and 0% complete growth inhibition.

| | | Relative length | |
|---|---|---|---|
| | Concentration | Roots | Roots + shoot |
| Control | — | 100 | 100 |
| Cl—CH$_2$—CH$_2$—P(=O)(OH)$_2$ | ½ mmol. | 40 | 42 |
| [Cl—CH$_2$—CH$_2$—N$^\pm$(CH$_3$)$_3$] Cl$^-$ | ½ mmol. | 100 | 101 |
| Cl—CH$_2$—CH$_2$—P(=O)(O$^-$)$_2$ · [Cl—CH$_2$—CH$_2$—N$^\pm$(CH$_3$)$_3$]$_2$ | 1 mmol. | 91 | 94 |
| | ½ mmol. | 34 | 34 |

EXAMPLE 12

The compounds of the invention were applied, under otherwise the same conditions, in a concentration of 200 ppm. The results are given below:

| | Relative length | |
|---|---|---|
| | Roots | Roots + shoot |
| Control | 100 | 100 |
| [Cl—CH$_2$—CH$_2$—N$^\pm$(CH$_3$)$_3$] Cl$^-$ | 84 | 90 |
| Cl—CH$_2$—CH$_2$—P(=O)(OH)(O$^-$) · Cl—CH$_2$—CH$_2$—N$^\pm$(CH$_3$)$_3$ | 38 | 34 |
| CH$_2$=CH—P(=O)(OH)(O$^-$) · Cl—CH$_2$—CH$_2$—N$^\pm$(CH$_3$)$_3$ | 38 | 34 |

|  | Relative length | |
| --- | --- | --- |
|  | Roots | Roots + shoot |
|  | 88 | 89 |
| 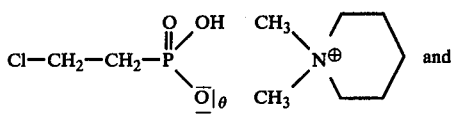 | 34 | 30 |
|  | 24 | 28 |
|  | 54 | 63 |
|  | 38 | 39 |
We claim:
1. A salt of a phosphonic acid, said salt being selected from the group consisting of
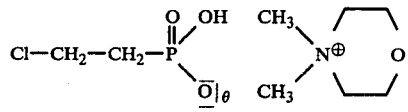 and
-continued
2. An agent for inhibiting plant growth, which agent contains, in aqueous solution, an effective amount of a salt as set forth in claim 1.
* * * * *